United States Patent [19]  [11] 4,239,767
Büchel et al.  [45] Dec. 16, 1980

[54] ANTIMYCOTIC DIARYLOXY-IMIDAZOLYL-O,N-ACETALS

[75] Inventors: Karl H. Büchel, Leverkusen; Wolfgang Krämer; Manfred Plempel, both of Wuppertal-Elberfeld, all of Fed. Rep. of Germany

[73] Assignee: Bayer Aktiengesellschaft, Fed. Rep. of Germany

[21] Appl. No.: 629,215

[22] Filed: Nov. 6, 1975

[30] Foreign Application Priority Data

Nov. 27, 1974 [DE] Fed. Rep. of Germany ....... 2455954

[51] Int. Cl.³ .................. A61K 31/415; C07D 233/60
[52] U.S. Cl. ................. 424/273 R; 548/341; 568/31; 568/43; 568/325; 568/333
[58] Field of Search ............ 260/309; 424/273, 273 R; 548/341

[56] References Cited

U.S. PATENT DOCUMENTS

| | | | |
|---|---|---|---|
| 3,647,815 | 3/1972 | Hegedus et al. | 260/309 |
| 3,833,603 | 9/1974 | Buchel et al. | 260/309 |
| 3,940,413 | 2/1976 | Kramer et al. | 260/309 |
| 3,940,414 | 2/1976 | Kramer et al. | 260/309 |
| 4,000,299 | 12/1976 | Krämer et al. | 548/341 X |

OTHER PUBLICATIONS

Wolf & Wolf–The Fungi, vol. II, pp. 365, 373 and 379 (1947), (John Wiley & Sons, Inc., N.Y.).
Meiser et al., Chem. Abst. 1975, vol. 82, No. 120068t.

*Primary Examiner*—Henry R. Jiles
*Assistant Examiner*—Richard A. Schwartz
*Attorney, Agent, or Firm*—Jacobs & Jacobs

[57] ABSTRACT

Diaryloxy-imidazolyl-O,N-acetals of the formula

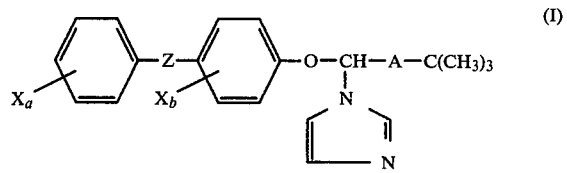

(I)

or pharmaceutically-acceptable, nontoxic salts thereof wherein
 X and Y are each halo, alkyl, alkoxy, haloalkylthio, nitro, amino, alkylamino or dialkylamino;
 Z is a direct bond, methylene, oxygen, sulphur, sulphonyl, alkoxymethylene or a keto moiety;
 A is a keto moiety or a moiety of the formula C(OH)R, wherein R is hydrogen or alkyl; and
 a and b are each integers from 0 to 3;
are useful for their antimycotic activity and their sporocidal action.

139 Claims, No Drawings

ANTIMYCOTIC DIARYLOXY-IMIDAZOLYL-O,N-ACETALS

The present invention is concerned with diaryloxyimidazolyl-O,N-acetals, a process for their production, pharmaceutical compositions embodying said compounds as the active agent, and methods of treating mycotic infections in humans and animals wherein said compounds are administered as the active agent.

It is known in the art that certain N-tritylimidazoles exhibit antimycotic activity: See Belgian Pat. No. 720,801 and U.S. Pat. Nos. 3,660,577, 3,839,573, 3,658,956, 3,655,899, 3,655,900, 3,657,442, 3,657,445, 3,660,576, 3,720,770, 3,705,172, 3,872,095, 3,711,498, 3,711,500, 3,717,657, 3,711,499 and 3,711,501.

It is also known in the art that imidazolyl-1-etherketones exhibit antimucotic activity: See German Offenlegungsschrift No. 2 105 490 and Belgian Pat. No. 804,092. However, those compounds do not exhibit a very broad spectrum of activity and, more importantly, they do not exhibit any sporocidal activity.

The present invention is directed to diaryloxyimidazolyl-O,N-acetals of the formula:

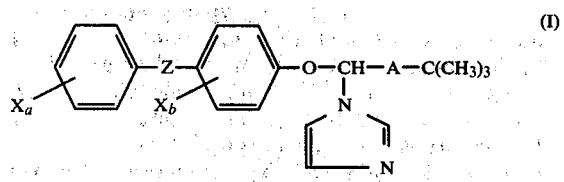

and pharmaceutically-acceptable, nontoxic salts thereof, wherein

X and Y are each halo, alkyl especially lower alkyl, alkoxy especially lower alkoxy, haloalkylthio especially halo(lower alkylthio) of up to 5 halo atoms, nitro, amino, alkylamino especially lower alkylamino, or dialkylamino especially di(lower alkylamino);

Z is a direct bond, methylene, oxygen, sulphur, sulphonyl, alkoxymethylene especially lower alkoxymethylene or a keto moiety;

A is a keto moiety or a moiety of the formula C(OH)R, wherein R is hydrogen or alkyl especially lower alkyl; and a and b are each integers from 0 to 3.

The compounds of the present invention may be obtained by reacting halogeno-ether-ketones of the formula:

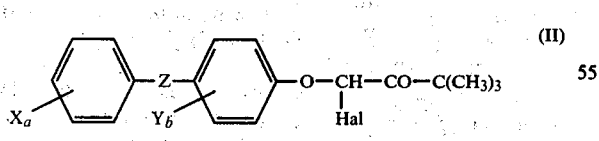

wherein

X, Y, Z, a and b are as above defined, and
Hal is chloro or bromo, with imidazole, if appropriate, in the presence of an acid binding agent, and, if appropriate, in the presence of a diluent, and, if appropriate, by reducing the imidazolylketone thereby obtained. This reduction step may be carried out in accordance with any of the following variants which are listed for convenience as variants 1 to 5 below:

1. With hydrogen in the presence of a catalyst and, optionally, in the presence of a polar solvent; or
2. With aluminum isopropylate in the presence of a solvent; or
3. With a complex hydride, optionally in the presence of a polar solvent; or
4. With formamidinesulphinic acid and an alkali metal hydroxide, optionally in the presence of a polar solvent; or
5. With an organo-metallic compound of the formula $$M-R \qquad (III),$$

wherein
R is as above defined and
M is an alkali metal or the moiety B-Mg, wherein B is chloro, bromo or iodo;

in the presence of an inert solvent.

The reduced compounds of formula (I) above have two asymmetric carbon atoms and they can therefore exist in both the erythro form and the threo form. In both instances, they are generally in the form or racemates.

According to one embodiment of the present invention

X and Y are each fluoro, chloro, bromo, alkyl of 1 to 4 carbon atoms, alkoxy of 1 to 4 carbon atoms, haloalkylthio of 1 to 4 carbon atoms in the alkyl moiety and up to 5 halo atoms, nitro, amino, alkylamino of 1 to 4 carbon atoms, or dialkylamino of 1 to 4 carbon atoms;

R is hydrogen or alkyl of 1 to 4 carbon atoms; and
a and b are each integers from 0 to 2.

According to another embodiment of the present invention

X and Y are each fluoro, chloro, bromo, methyl, ethyl, isopropyl, t-butyl, alkoxy of 1 or 2 carbon atoms, haloalkylthio of 1 or 2 carbon atoms in the alkyl moiety and up to 3 halo atoms selected from the group consisting of fluoro and chloro, nitro, amino, alkylamino of 1 or 2 carbon atoms or dialkylamino of 1 or 2 carbon atoms.

According to another embodiment of the present invention

X and Y are each fluoro, chloro, bromo, methyl, ethyl, isopropyl, t-butyl, methoxy, trifluoromethylthio, nitro, amino, ethylamino or dimethylamino; and a and b are each 0 to 2.

According to another embodiment of the present invention

X and Y are each chloro, bromo or nitro;
Z is a direct bond, methylene, sulphonyl, alkoxymethylene of 1 to 4 carbon atoms in the alkoxy moiety or CO;
A is CO or the moiety C(OH)R, wherein R is hydrogen or alkyl of 1 to 4 carbon atoms;
a is 0 or 1; and
b is 0, 1 or 2.

According to another embodiment of the present invention a and b are each 0.

According to another embodiment of the present invention a is 1 and b is 0.

The preferred salts according to the present invention are those formed from acids such as the hydrogen halide acids, for example, hydrochloric acid or hydrobromic acid, especially hydrochloric acid; phosphoric acid; nitric acid; sulfuric acid; monofunctional and bifunctional carboxylic acids and hydroxycarboxylic acids, such as acetic acid, maleic acid, succinic acid, fumaric acid, tartaric acid, citric acid, salicylic acid, sorbic acid, lactic acid and 1,5-naphthalene disulphonic acid. Thus, the preferred salts include the hydrogen halides, such as the hydrochloride and hydrobromide, especially the hydrochloride; the phosphate; nitrate; sulphate; acetate; maleate; succinate, fumarate; tartrate; citrate, salicylate, sorbate, lactate; and 1,5-naphthalene disulphonate.

The compounds of the present invention are particularly useful for their strong and broad antimycotic activity and the sporocidal activity which they exhibit which is not present in such commercially available products as Griseofulvin and Nystatin.

If 1-bromo-1-(4'-phenylsulphonyl-phenoxy)-3,3-dimethylbutan-2-one and imidazole are used as starting materials, the course of the reaction can be represented by the following equation:

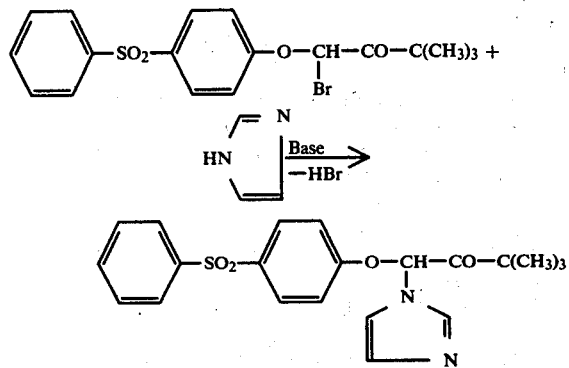

The reduction reactions will be illustrated with two examples:

If 1-[imidazolyl-(1)]-1-(4'-phenylsulphonyl-phenoxy)-3,3-dimethylbutan-2-one and hydrogen are used as starting materials, the course of the reaction can be represented by the following equation:

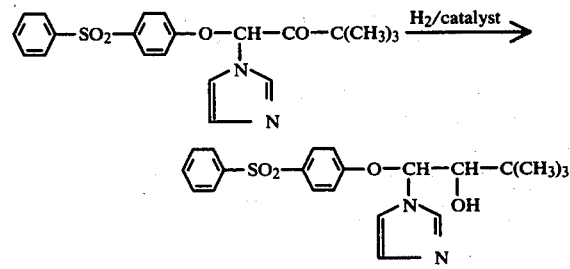

If 1-[4'-(4''-chlorophenyl)-phenoxy]-1-[imidazolyl(1)]-3,3-dimethylbutan-2-one and methylmagnesium iodide are used as starting materials, the course of the reaction can be represented by the following equation:

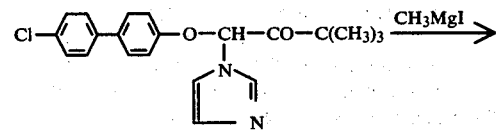

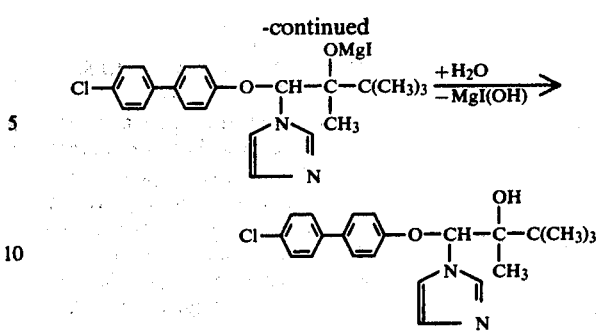

The reactions with other reducing agents are similar to those described above and proceed in an analogous manner.

The following starting materials are representative of those compounds of the formula (II):

1-bromo-1-[4'-(3''-methylphenyl)-phenoxy]-3,3-dimethylbutan-2-one, 1-bromo-1-[4'-(2''-chlorophenyl)-(3'-chlorophenoxy)]-3,3-dimethyl-butan-2-one, 1-bromo-1-[4'-(2''-bromo-4''-chlorophenyl)-(2'-bromophenoxy)]-3,3-dimethylbutan-2-one, 1-chloro-1-[4'-(4''-nitrophenyl)-(2',6'-dichlorophenoxy)]-3,3-dimethylbutan-2-one, 1-chloro-1-[4'-(4''-ethoxyphenyl)-(2'-bromo-6'-chlorophenoxy)]-3,3-dimethylbutan-2-one, 1-chloro-1-[4'-(3''-aminophenyl)-(2'-methylphenyl)]-3,3-dimethylbutan-2-one, 1-chloro-1-[4'-(2''-methylphenoxy)-(2'-chlorophenoxy)]-3,3-dimethylbutan-2-one, 1-chloro-1-[4'-(3''-chlorophenoxy)-phenoxy]-3,3-dimethylbutan-2-one, 1-chloro-1-[4'-phenoxy-2',6'-dibromophenoxy]-3,3-dimethylbutan-2-one, 1-bromo-1-[4'-(3''-nitrophenylthio)-(2'-bromophenoxy)]-3,3-dimethylbutan-2-one, 1-bromo-1-[4'-(2''-methoxyphenylthio)-(2'-chlorophenoxy)]-3,3-dimethylbutan-2-one, 1-bromo-1-[4'-(4''-bromophenylthio)-(3'-chlorophenoxy)]-3,3-dimethylbutan-2-one, 1-bromo-1-[4'-(2''-chlorophenylsulphonyl)-phenoxy]-3,3-dimethylbutan-2-one, 1-bromo-1-[4'-(4''-ethylphenylsulphonyl)-(2',6'-dichlorophenoxy)]-3,3-dimethylbutan-2-one, 1-chloro-1-[4'-(2''-chlorophenoxycarbonyl)-(2'-bromophenoxy)]-3,3-dimethylbutan-2-one, 1-chloro-1-[4'-(2'',6''-dichlorophenylcarbonyl)-(2'-chlorophenoxy)]-3,3-dimethylbutan-2-one, 1-chloro-1-[4'-(2''-nitrophenylcarbonyl)-phenoxy]-3,3-dimethylbutan-2-one, 1-chloro-1-[4'-(4''-bromobenzyl)-(3'-bromophenoxy)]-3,3-dimethylbutan-2-one, 1-chloro-1-[4'-(4''-trifluoromethylthiobenzyl)-(2',3'-dichlorophenoxy)]-3,3-dimthylbutan-2-one, 1-chloro-1-[4'-(3'',5''-dichlorobenzyl)-(2'-methylphenoxy)]-3,3-dimethylbutan-2-one, 1-bromo-1-[4'-(4''-tert-.butylbenzyl)-phenoxy]-3,3-dimethylbutan-2-one and 1-bromo-1-[4'-(2''-ethylaminobenzyl)-(2'-nitrophenoxy)]-3,3-dimethylbutan-2-one.

The halogeno-ether-ketones of the formula (II) which are used as starting materials are not previously know per se but can be prepared according to processes which are per se known; for example, by reacting a compound of the formula

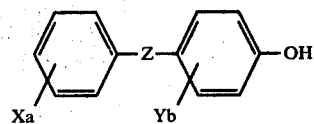

(IV)

wherein

X, Y, Z, a and b are as above defined, with a haloenoketone of the formula

$$\text{Hal-CH}_2\text{-CO-C(CH}_3)_3 \qquad (V),$$

wherein Hal is halo, preferably chloro or bromo. The active hydrogen atom which still remains is subsequently replaced by halogen in the usual manner. (See also the examples below.)

Diluents which can be used for the reaction according to the invention are preferably polar organic solvents. These preferentially include nitriles; such as acetonitrile; sulphoxides, such as dimethylsulphoxide; formamides, such as dimethylformamide; ketones, such as acetone; ethers, such as diethyl ether and tetrahydrofurane; nitroalkanes, such as nitriomethane, and unsymmetrical chlorohydrocarbons, such as methylene chloride and chloroform.

The reaction may be carried out in the presence of an acid-binding agent. All inorganic and organic acid-binding agents which can usually be employed can be added, such as alkali metal carbonates, for example sodium carbonate, potassium carbonate or sodium bicarbonate, or such as lower tertiary alkylamines, cycloalkylamines or aralkylamines, for example triethtylamine and dimethylbenzyl-cyclohexylamine, or such as pyridine and diazabicyclooctane. The use of an appropriate excess of imidazole is preferred.

The reaction temperatures can be varied within a substantial range. In general, the reaction is carried out at between about 20° and about 150° C., preferably at 60° to 120° C. If a solvent is used, the reaction is suitably carried out at the boiling point of the particular solvent.

In carrying out the process according to the invention, preferably 2 mols of imidazole and 1 mol of acid-binding agent are employed per mol of the compounds of the formula (II). Amounts of up to about 20% above or below these can be used. To isolate the compounds of the formula (I), the solvent is distilled off, the residue is taken up in an organic solvent and the solution is washed with water. The organic phase is dried over sodium sulphate and freed from the solvent in vacuo. The residue is purified by distillation or recrystallization.

Diluents which can be used for the reduction according to the invention, in accordance with variant 1, are polar organic solvents. These preferentially include alcohols, such as methanol and ethanol, and nitriles, such as acetonitrile. The reaction is carried out in the presence of a catalyst. Preferably, noble metal catalysts, noble metal oxide (or noble metal hydroxide) catalysts or so-called "Raney catalysts" are used, especially platinum, or platinum oxide and nickel. The reaction temperatures can be varied within a substantial range. In general, the reaction is carried out at between 20° and 50° C., preferably at 20° to 40° C. The reaction can be carried out under normal pressure, but also under elevated pressure (for example 1 to 2 atmospheres gauge). In the reaction according to variant 1, about 1 mol of hydrogen and 0.1 mol of catalyst are employed per mol of the compound of the formula (II); to isolate the compounds, the catalyst is filtered off, the solution is freed from the solvent in vacuo and the resulting products of the formula (I) are purified by distillation or recrystallization. If desired, the salts of the compounds according to the invention are obtained according to customary methods.

If reduction variant 2 is followed, suitable diluents for the reaction according to the invention are preferentially alcohols, such as isopropanol, or inert hydrocarbons, such as benzene. Again, the reaction temperatures can be varied within a substantial range. In general, the reaction is carried out at between 20° C. and 120° C., preferably at 50° C. to 100° C. To carry out the reaction, about 1 to 2 mols of aluminum isopropylate are employed per mol of compound of the formula (II). To isolate the compound of the formula (I), the excess solvent is removed by distillation in vacuo and the aluminum compound which has been produced is decomposed with dilute sulphuric acid or sodium hydroxide solution. The further work-up is carried out in the usual manner.

If reduction variant 3 is followed, diluents which can be used for the reaction according to the invention are polar organic solvents. These preferentially include alcohols, such as methanol, ethanol, butanol and isopropanol, and ethers, such as diethyl ether or tetrahydrofurane. The reaction is, in general carried out at 0° C. to 30° C., preferably at 0° C. to 20° C. For this reaction, about 1 mol of a complex hydride, such a sodium borohydride or lithium alanate, are employed per mol of the compound of the formula (II). To isolate the compounds of the formula (I), the residue is taken up in dilute hydrochloric acid, the solution is then rendered alkaline and the product is extracted with an organic solvent. The further work-up is carried out in the usual manner.

Diluents which can be used for the reduction according to the invention, in accordance with reduction variant 4, are polar organic solvents, preferably alcohols, such as methanol and ethanol, but also water. The reaction temperatures can here again be varied within a substantial range: The reaction is carried out at temperatures of between 20° C. and 100° C., preferably at 50° C. to 100° C. To carry out the reaction, about 1 to 3 mols of formamidinesulphinic acid and 2 to 3 mols of alkali metal hydroxide are employed per mol of the compounds of the formula (II). To isolate the end products, the reaction mixture is freed from the solvent and the residue is extracted with water and organic solvents, worked-up in the usual manner and purified.

In the reduction according to the present invention, in accordance with reduction variant 5, compounds of the formula (I) in which R is not hydrogen are obtained. The organo-metallic compounds required for this purpose are described by the formula (III). R is preferably alkyl of 1 to 6, especially of 1 to 4, carbon atoms. M in the formula (III) is preferably lithium, sodium, and the so-called "Grignard grouping Mg-B", in which B is chloro, bromo or iodo. The organo-metallic compounds of the formula (III) are generally known. (A summary and survey of numerous publications is to be found, for example, in G. E. Coates, *Organo-Metallic Compounds*, 2nd edition, Methuen and Co., London (1960).)

For the reduction according to the present invention, in accordance with reduction variant 5, suitable diluents are preferably anhydrous ethers, such as diethyl ether and dibutyl ether, as well as tetrahydrofurane. The reaction temperatures can be varied between 0° C. and 80° C., preferably between 30° C. and 60° C. In carrying out the reaction, about 1 mol of the organo-metallic compound of the formula (III) is employed per mol of the compounds of the formula (II). The mixtures obtained by organo-metallic reactions are worked-up in the usual and generally known manner.

The pharmaceutically-acceptable, nontoxic salts of the present invention can be obtained in accordance with standard procedure for salt formation; for example, by dissolving the base formed in ether, for example, diethyl ether, and adding the appropriate acid, such as, for example, hydrogen chloride, followed by isolation according to standard techniques, for example, by filtration and purification, if desired.

The broad spectrum of antimycotic activity of the compounds of the present invention is characterized by activity against dermatophytes in yeast and also against biphase fungi in molds. In contrast to other known azole antimycotics and commercially available products such as Griseofulvin, Nystatin, Pimericin or 5-Fluorocytosin, the compounds of the present invention exhibit good sporocidal activity against micro- and macro-conidia of dermatophytes, as well as conidiospores of *Aspergillus fumigatus*.

The following are illustrative of the fields of use for human medicine: dermatomycoses and systemic mycoses caused by *Trichophyton mentagrophytes* and other species of Trichophyton, species of *Microsporon, Epidermophyton floccosum*, blastomyces and biphase fungi, as well as molds.

The following may be mentioned as illustrative fields of use in veterinary medicine: all dermatomycoses and systemic mycoses, especially those caused by the above-mentioned pathogens.

The pharmaceutical compositions of the present invention contain a major or minor amount, e.g., 0.1% to 99.5%, preferably 0.5% to 95%, of active ingredient as above defined, in combination with a pharmaceutically-acceptable, nontoxic, inert diluent or carrier, the carrier comprising one or more solid, semi-solid or liquid diluent, filler and formulation adjuvant which is nontoxic, inert and pharmacetically-acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 10 to about 300, preferably 500 to 200, mg/kg of body weight per day. In some instances a sufficient therapeutic effect can be obtained at a lower dose, while in others a larger dose will be required.

Oral administration can be effected utilizing solid and liquid dosage unit forms such as powders, tablets, dragees, capsules, granlates, suspensions, solutions and the like.

Powders are prepared by comminuting the compound to a suitable fine size and mixing with a similarly comminuted pharmaceutical carrier such as an edible carbohydrate as, for example, starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants, such as colloidal silica, talc, magnesium stearate, calcium stearate or solid polyethylene glycol can be added to the powder mixture before the filling operation. A disintegrating or solubilizing agent, such as agar-agar, calcium carbonate or sodium carbonate, can be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably communited, with a diluent or base, as described above, and, optionally, with a binder, such as carboxymethyl cellulose, an alginate, gelatin or polyvinyl pyrrolidone, a solution retardant, such as paraffin, a resorption accelerator, such as a quaternary salt and/or an absorption agent, such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution, while elixirs are prepared through the use of a nontoxic alcoholic vehicle. Suspensions can be formulated by dispersing the compound in a nontoxic vehicle. Solubilizers and emulsifiers such ethoxylated isostearyl alcohols and polyoxyethylene sorbitol esters, preservatives, flavor additives such as peppermint oil or saccharin, and the like, can also be added.

Where appropriate, dosage unit formulations for oral administration can be microencapsulated. The formulation can also be prepared to prolong or sustain the release, as for example, by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection, such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids, such as polyethylene glycol, cocoa butter, higher esters, as for example, for myristyl palmitate, or mixtures thereof.

Topical administration can be effected utilizing solid dosage unit forms such as powders or liquid or semi-liquid dosage unit forms, such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols, such as isopropanol, and the like. Other excipients, such as emulsifiers, preservatives, colorants, perfumes and the like, can also be present. Formulations can also be administered as an aerosol, utilizing the usual propellants, such as the chlorofluoro-hydrocarbons.

The preferred daily dose is 500 mg to 30 g of active agent.

While the routes of administration include oral, parenteral (i.e., intramuscular, intraperitoneal and intravenous), rectal and topical, parenteral administration is particularly preferred.

The preferred pharmaceutical compositions are therefore those in a form suitable for parenteral administration such as solutions and suspensions.

The antimycotic activity of the compounds of the present invention is exemplified by the following in vitro and in vivo data.

The compounds of the present invention were well tolerated and effective antimycotics exhibiting a broad spectrum of activity on oral administration, parenteral administration and topical application. If the duration of treatmment is ten days, the sporocidal action is, with few exceptions, greater than 99%.

1.) in vitro activity

The in vitro test was carried out as a series dilution test. Amount inoculated: $10^3$ germs/ml. The nutrient substrates used were Sabouraud's milieu d'epreuve, meat stock/glucose bouillon, malt extract agar and Francis's blood agar. The incubation temperature was 28° C. and the incubation time 24–96 hours.

| Preparation | in γ/ml MIC values when used against | | | | |
|---|---|---|---|---|---|
| | Trich. ment. | Cand. alb. | Asp. fum. | Torulopsis glab. | Sporothrix Schenckii |
| Cl—⟨⟩—⟨⟩—O—CH—CH—C(CH₃)₃ with N-imidazole and OH | <1 | 4 | 2–4 | 4 | 0.1 |
| ⟨⟩—CH₂—⟨⟩—O—CH—CH—C(CH₃)₃ with N-imidazole and OH | <1 | 4 | <1 | 4 | 0.5 |
| ⟨⟩—SO₂—⟨⟩—O—CH—CH—C(CH₃)₃ with N-imidazole and OH | <1 | 2–4 | <1 | 4 | 0.5 |
| Br—⟨⟩—⟨⟩(Cl,Cl)—O—CH—CO—C(CH₃)₃ with N-imidazole | 4 | 8 | 4 | 2 | 0.1 |
| ⟨⟩—CH₂—⟨⟩—O—CH—CO—C(CH₃)₃ with N-imidazole | <1 | 16 | 2 | 4 | 2 |
| ⟨⟩—SO₂—⟨⟩—O—CH—CO—C(CH₃)₃ with N-imidazole | 64 | 4 | 1 | 2 | 2 |

| Preparation | in γ/ml MIC values when used against | | | | |
|---|---|---|---|---|---|
| | Trich. ment. | Cand. alb. | Asp. fum. | Torulopsis glab. | Sporothrix Schenckii |
| 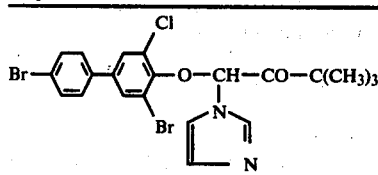 | 8 | 8 | 4 | 4 | 4 |

2.) in vivo activity

The table which follows summarizes in the vivo action of the preparations claimed on oral administration—for the models of candidosis of mice and trichophytia of mice—and on local administration—for the model of trichophytia of guinea-pigs.

| | Therapeutic activity | | |
|---|---|---|---|
| | on oral administration of 100 mg/kg of body weight, twice daily | | on local application of a 1% strength solution once a day from the 3rd to the 13th day after infection |
| Preparation | candidosis % survival | trichophytia | |
| Control | 5 | pronounced dermatophytosis | pronounced dermatophytosis |
| 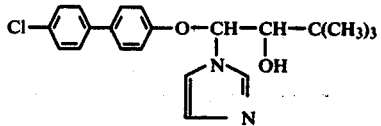 | 80 | +++ | ++++ |
| 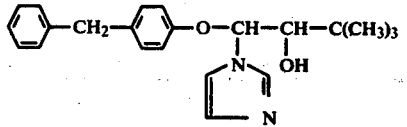 | 60 | ++ | +++ |
| 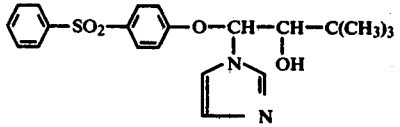 | 80 | ++ | +++ |
| 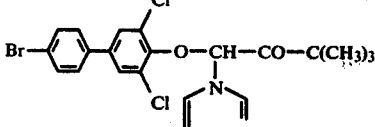 | 50 | ++ | +++ |
| 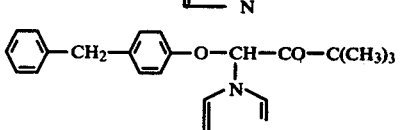 | 50 | +++ | ++ |
| 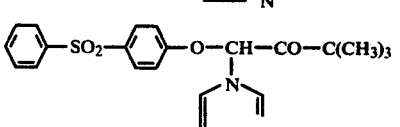 | 80 | ++ | +++ |
| 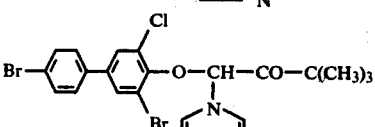 | 40 | + | ++ |

++++ very good action = no sign of infection
+++ good action = very slight sign of infection
++ action = slight loss of hair
+ slight action = loss of hair, squamation

(3.) Toxicity, and toleration by the skin

On oral administration to mice and rats, the preparations of the present invention showed an $LD_{50}$ averaging 400–700 mg/kg of body weight. 1% strength solutions are well tolerated by skin.

(4.) Sporocidal action

Spore suspensions: stated incubation times and spread homogeneously on malt extract Petri dishes, and the number of spores which still germinate is counted, after 48 hours' incubation time at 28° C., in comparison to untreated controls. The table which follows lists, for the individual preparations, the number of spores which still germinate after an exposure period of 72 hours at preparation concentrations of 10 γ/ml.

| Preparation | Number of spores still capable of germination after exposure to 10 γ of preparation/ml for a period of 72 hours | |
|---|---|---|
| | Trich. ment. | Aspergillus fum. |
| Control | $10^5$ = mycelium | $10^5$ = mycelium |
| Cl—C₆H₄—C₆H₄—O—CH(N-vinyl-imidazolyl)—CH(OH)—C(CH₃)₃ | 80 | 35 |
| C₆H₅—CH₂—C₆H₄—O—CH(N-vinyl-imidazolyl)—CH(OH)—C(CH₃)₃ | 110 | 40 |
| C₆H₅—SO₂—C₆H₄—O—CH(N-vinyl-imidazolyl)—CH(OH)—C(CH₃)₃ | 60 | 70 |
| Br—C₆H₄—C₆H₂(Cl)(Cl)—O—CH(N-vinyl-imidazolyl)—CO—C(CH₃)₃ | 90 | 40 |
| C₆H₅—CH₂—C₆H₄—O—CH(N-vinyl-imidazolyl)—CO—C(CH₃)₃ | 40 | 60 |
| C₆H₅—SO₂—C₆H₄—O—CH(N-vinyl-imidazolyl)—CO—C(CH₃)₃ | $10^5$ = mycelium | 70 |
| Br—C₆H₄—C₆H₂(Cl)(Br)—O—CH(N-vinyl-imidazolyl)—CO—C(CH₃)₃ | 60 | 45 |

In contrast to other azole antimycotics, the compounds of the present invention exhibit a sporocidal activity against micro-conidia and macro-conidia of Dermatophytes and against conidiospores of *Aspergillus fumigatus*.

Experimental method

About $10^4$ spores of *Trich. ment.* or *Trich. Quinckeanum* or *Aspergillus fumigatus* per ml are suspended in physiological NaCl solution and the stated preparations are added in concentrations of 1, 5, 10, 50 and 100 y/ml of suspending solution. The spore suspensions are incubated for 24, 48, 72, 96, 120 and 240 hours, 0.1 ml are withdrawn per concentration and per tube after the According to this result, more than 90% of the inocubated spores are killed under the stated experimental conditions. For a period of exposure of 10 days, the sporocidal action of the preparations is, with one exception, greater than 99%.

The following nonlimitative examples more particularly illustrate the present invention:

PREPARATION EXAMPLES

EXAMPLE 1

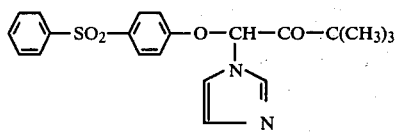

44 g (0.107 mol) of 1-bromo-1-(4'-phenylsulphonyl-phenoxy)-3,3-dimethylbutan-2-one in 500 ml of absolute acetonitrile are heated with 34 g (0.5 mol) of imidazole for 26 hours under reflux. The solvent is then distilled off in a waterpump vacuum and the residue is taken up in 100 ml of water. The resulting precipitate is washed with twice 100 ml of water and recrystallized from benzene. 26 g (66% of theory) of 1-[imidazolyl-(1)]-1-(4'-phenylsulphonylphenoxy)-3,3-dimethylbutan-2-one of melting point 146° C. are obtained.

Starting material

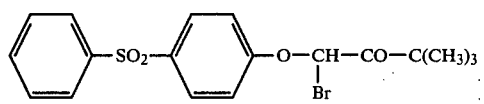

49 g of bromine are added dropwise to 99.6 g (0.3 mol) of 1-4'-phenylsulphonyl-phenoxy)-3,3-dimethylbutan-2-one, suspended in 600 ml of carbon tetrachloride, at room temperature. After the mixture has lost its color, the precipitate formed is filtered off, washed with petroleum ether and recrystallized from benzene. 89 g (72% of theory) of 1-bromo-1-(4'-phenylsulphonyl-phenoxy)-3,3-dimethylbutan-2-one of melting point 157°–162° C. are obtained.

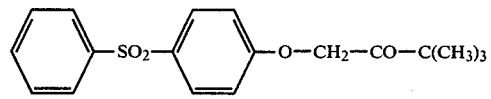

280 g (2 mols) of powdered potassium hydroxide are suspended in 2 liters of methyl ethyl ketone. 467 g (2 mols) of 4-phenylsulphonyl-hydroxyphenyl are added and the mixture is heated to the boil. Thereafter 269 g (2 mols) of α-chloropinacolone are added dropwise over the course of 1 hour and the mixture is heated for 15 hours under reflux. After cooling, the solid residue is filtered off, washed and recrystallized from ligroin. 687 g (85% of theory) of 1-(4'-phenylsulphonyl-phenoxy)-3,3-dimethylbutan-2-one of melting point 105°–108° C. are obtained.

EXAMPLE 2

(Reduction according to variant 3)

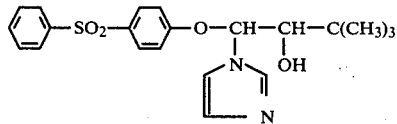

1.6 g (0.042 mol) of sodium borohydride are added in portions to 11 g (0.028 mol) of 1-[imidazolyl-(1)]-(4'-phenylsulphonyl-phenoxy)-3,3-dimethylbutan-2-one, suspended in 100 ml of methanol, at −5° C. The mixture is stirred for 17 hours at room temperature. Thereafter 6.5 ml of concentrated hydrochloric acid are added to the reaction mixture and the whole is again stirred for 17 hours at room temperature. It is then extracted by shaking with three times 200 ml of methylene chloride. The combined organic phases are dried over sodium sulphate. The solvent is distilled off in a waterpump vacuum. 50 ml of n-pentane are added to the residue and the crystals are filtered off. 10 g (90% of theory) of 1-[imidazolyl-(1)]-(4'-phenylsulphenyl-phenoxy)-3,3-dimethylbutan-2-ol of melting point 198° C. are obtained.

EXAMPLE 3

(Reduction according to variant 5)

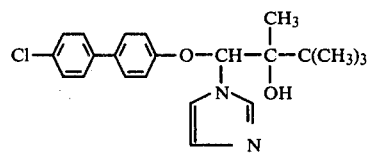

2.4 g (0.1 mol) of magnesium filings are suspended in 30 ml of ether. A solution of 14.2 g (0.1 mol) of methyl iodide in 50 ml of absolute ether is added dropwise. After 2 hours, a solution of 18.4 g (0.05 mol) of 1-[4'-(4''-chlorophenyl)-phenoxy]-1-[imidazolyl-(1)]-3,3-dimethylbutan-2-one in 100 ml of absolute tetrahydrofurane is added dropwise at 10° C. and the mixture is stirred for a further 15 hours at room temperature. Thereafter, the reaction mixture is stirred, at 0° C., into a solution of 10 g of ammonium chloride in 500 ml of water and the mixture is left to stand overnight. The ether phase is separated off, washed with twice 100 ml of water and dried over sodium sulphate, and the solvent is distilled off in a waterpump vacuum. An oil remains, which crystallizes on trituration with hot petroleum ether. It is recrystallized from 40 ml of ethyl acetate. 16.6 g (86% of theory) of 1-[4'-(4''-chlorophenyl)-phenoxy]-1-[imidazolyl-(1)]-2-methyl-3,3-dimethylbutan-2-ol of melting point 177° C. are obtained.

EXAMPLE 4

(salt formation)

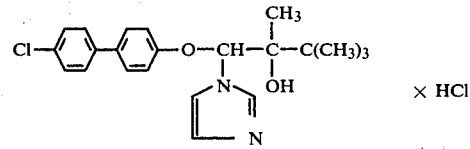

5 g (0.013 mol) of 1-[4'-(4''-chlorophenyl)-phenoxy]-1-[imidazolyl-(1)]-2-methyl-3,3-dimethylbutan-2-ol are dissolved in 25 ml of acetone and 25 ml of methylene chloride. 20 ml of hydrochloric acid in ether are added thereto, the solvent is distilled off in a waterpump vacuum and the residue is boiled up with acetone. 4.7 g (86% of theory) of 1-4'-(4''-chlorophenyl)-phenoxy]-1-[imidazolyl-(1)]-2-methyl-3,3-dimethylbutan-2-ol hydrochloride of melting point 220°–224° C. (with decomposition) are obtained.

Table 1 below sets forth the compounds of Examples 5 through 20 which are produced in a manner analogous to Examples 1 to 4 from the reactants set forth in Table 2.
TABLE 1
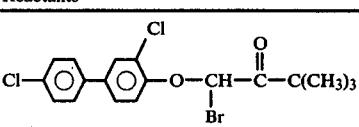
| Example No. | X | a | Y | b | Z | A | Melting point (°C.) |
|---|---|---|---|---|---|---|---|
| 5 | 4-Cl | 1 | 2-Cl | 1 | — | CO | 102–104 |
| 6 | 4-Cl | 1 | 2-Cl | 1 | — | CO | 67–100 (× HCl) |
| 7 | 4-Br | 1 | 2,6-Cl$_2$ | 2 | — | CO | 132–134 |
| 8 | — | 0 | — | 0 | —CH$_2$— | CO | 82 |
| 9 | 4-Br | 1 | 2-Br,6-Cl | 2 | — | CO | 127–129 |
| 10 | — | 0 | — | 0 | —O— | CO | 94–97 |
| 11 | — | 0 | — | 0 | —O— | CO | 151 (× HCl) |
| 12 | 4-NO$_2$ | 1 | — | 0 | — | CO | 180–181 (× HCl) |
| 13 | — | 0 | — | 0 | —CO— | CO | 128 |
| 14 | 4-Cl | 1 | — | 0 | — | CHOH | 132–133 |
| 15 | 4-Cl | 1 | — | 0 | — | CHOH | 173–177 (× H$_2$SO$_4$) |
| 16 | 4-Cl | 1 | — | 0 | — | CHOH | 187–192 (× HCl) |
| 17 | 4-Cl | 1 | — | 0 | — | CHOH | 158–164 (× 2H$_3$PO$_4$) |
| 18 | 4-Cl | 1 | — | 0 | — | CHOH | 145–150 (× HNO$_3$) |
| 19 | — | 0 | — | 0 | —CH$_2$— | CHOH | 142 |
| 20 | — | 0 | — | 0 | —CH— \| OCH$_3$ | CHOH | 120–124 |
TABLE 2
| Example No. | Reactants |
|---|---|
| 5 | 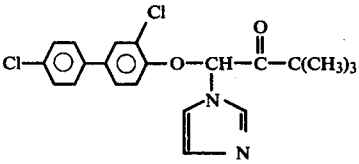 |
| 6 | 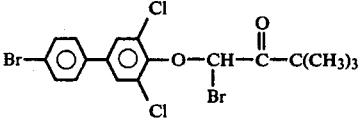 |
| 7 | 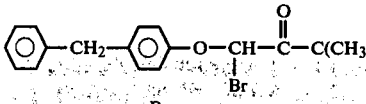 |
| 8 | 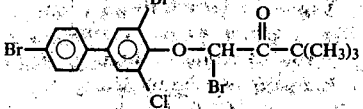 |
| 9 | 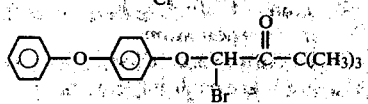 |
| 10 | 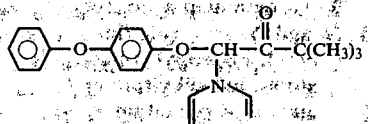 |
| 11 | 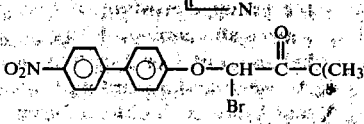 |
| 12 |  |

TABLE 2-continued

| Example No. | Reactants |
|---|---|
| 13 | ![structure] |
| 14 | ![structure] |
| 15 | ![structure] |
| 16 | ![structure] |
| 17 | ![structure] |
| 18 | ![structure] |
| 19 | ![structure] |
| 20 | ![structure] |

What is claimed is:

1. A compound of the formula

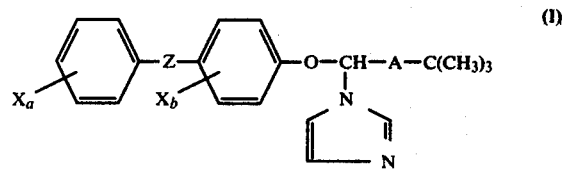

(I)

or a pharmaceutically acceptable, nontoxic salt thereof, wherein

X and Y are each halo, lower alkyl, lower alkoxy, halo(lower alkylthio), nitro, amino, lower alkylamino or di(lower alkyl) amino;

Z is methylene, oxygen, sulphur, sulphonyl, lower alkoxymethylene or a keto moiety;

A is a keto moiety or the moiety C(OH)R, wherein R is hydrogen or lower alkyl; and a and b are each integers from 0 to 3.

2. A compound according to claim 1 wherein
X and Y are each fluoro, chloro, bromo, alkyl of 1 to 4 carbon atoms, alkoxy of 1 to 4 carbon atoms, haloalkylthio of 1 to 4 carbon atoms in the alkyl moiety and up to 5 halo atoms, nitro, amino, alkylamino of 1 to 4 carbon atoms, or dialkylamino of 1 to 4 carbon atoms;
R is hydrogen or alkyl of 1 to 4 carbon atoms; and
a and b are each integers from 0 to 2.

3. A compound according to claim 1 wherein
X and Y are each fluoro, chloro, bromo, methyl, ethyl, isopropyl, t-butyl, alkoxy of 1 or 2 carbon atoms, haloalkylthio of 1 or 2 carbon atoms in the alkyl moiety and up to 3 halo atoms selected from the group consisting of fluoro and chloro, nitro, amino, alkylamino of 1 or 2 carbon atoms or dialkylamino of 1 or 2 carbon atoms.

4. A compound according to claim 1 wherein
X and Y are each chloro, bromo or nitro;

Z is methylene, sulphonyl, alkoxymethylene of 1 to 4 carbon atoms in the alkoxy moiety or CO;

A is CO or the moiety C(OH)R, wherein R is hydrogen or alkyl of 1 to 4 carbon atoms;

a is 0 or 1; and b is 0, 1 or 2.

5. A compound according to claim 4 wherein a and b are each 0.

6. A compound according to claim 4 wherein a is 1 and b is 0.

7. A compound according to claim 1 in the form of a salt wherein said salt is selected from the group consisting of a hydrohalide, phosphate, nitrate, sulfate, acetate, maleate, succinate, fumarate, tartrate, citrate, salicylate, sorbate, lactate and 1,5-naphthalene disulfonate.

8. The compound according to claim 1 which is

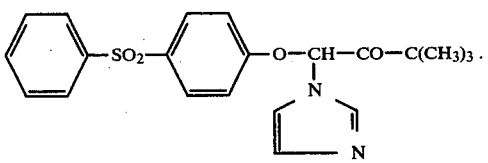

9. The compound according to claim 1 which is

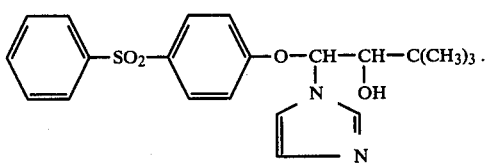

10. The compound according to claim 1 wherein Z is methylene, A is CO, and a and b are each 0.

11. The compound according to claim 1 wherein Z is oxygen, A is CO, and a and b are each 0.

12. The compound according to claim 1 wherein Z is oxygen, A is CO, and a and b are each 0, in the form of the hydrochloride salt.

13. The compound according to claim 1 wherein Z is CO, A is CO and a and b are each 0.

14. The compound according to claim 1 wherein Z is methylene, A is CHOH, and a and b are each 0.

15. The compound according to claim 1 wherein Z is

A is CHOH and a and b are each 0.

16. A compound according to claim 1 wherein Z is methylene.

17. A compound according to claim 1 wherein Z is methylene and a and b are each 0.

18. A compound according to claim 1 wherein Z is methylene, a is 0 and b is 1, 2 or 3.

19. A compound according to claim 1 wherein Z is methylene, a is 1, 2 or 3 and b is 0.

20. A compound according to claim 1 wherein Z is oxygen.

21. A compound according to claim 1 wherein Z is oxygen and a and b are each 0.

22. A compound according to claim 1 wherein Z is oxygen, a is 0 and b is 1, 2 or 3.

23. A compound according to claim 1 wherein Z is oxygen, a is 1, 2 or 3 and b is 0.

24. A compound according to claim 1 wheren Z is sulphur.

25. A compound according to claim 1 wherein Z is sulphur and a and b are each 0.

26. A compound according to claim 1 wherein Z is sulphur, a is 0 and b is 1, 2 or 3.

27. A compound according to claim 1 wherein Z is sulphur, a is 1, 2 or 3 and b is 0.

28. A compound according to claim 1 wherein Z is sulphonyl.

29. A compound according to claim 1 wherein Z is sulphonyl, and a and b are each 0.

30. A compound according to claim 1 wherein Z is sulphonyl, a is 0 and b is 1, 2 or 3.

31. A compound according to claim 1 wherein Z is sulphonyl, a is 1, 2 or 3 and b is 0.

32. A compound according to claim 1 wherein Z is lower alkoxymethylene.

33. A compound according to claim 1 wherein Z is lower alkoxymethylene and a and b are each 0.

34. A compound according to claim 1 wherein Z is lower alkoxymethylene, a is 0 and b is 1, 2 or 3.

35. A compound according to claim 1 wherein Z is lower alkoxymethylene, a is 1, 2 or 3 and b is 0.

36. A compound according to claim 1 wherein Z is a keto moiety.

37. A compound according to claim 1 wherein Z is a keto moiety and a and b are each 0.

38. A compound according to claim 1 wherein Z is a keto moiety, a is 0 and b is 1, 2 or 3.

39. A compound according to claim 1 wherein Z is a keto moiety, a is 1, 2 or 3 and b is 0.

40. A compound according to claim 2 wherein a and b are each 0.

41. A compound according to claim 2 wherein a is 1 or 2 and b is 0.

42. A compound according to claim 2 wherein a is 0 and b is 1 or 2.

43. A compound according to claim 3 wherein a and b are each 0.

44. A compound according to claim 3 wherein a is 1 or 2 and b is 0.

45. A compound according to claim 3 wherein a is 0 and b is 1 or 2.

46. A compound according to claim 4 wherein a is 0 and b is 1 or 2.

47. A compound according to claim 4 wherein a is 1 and b is 0, 1 or 2.

48. A compound according to claim 7 wherein a and b are each 0.

49. A compound according to claim 7 wherein a is 0 and b is 1, 2 or 3.

50. A compound according to claim 7 wherein a is 1, 2 or 3 and b is 0.

51. A pharmaceutical composition useful for treating mycoses in humans and animals which comprises an anti-mycotically effective amount of a compound of the formula

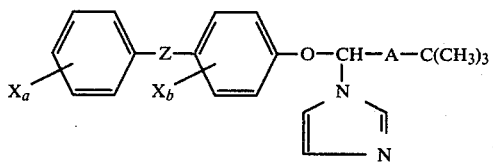
(I)

or a pharmaceutically acceptable, nontoxic salt thereof, wherein
X and Y are each halo, lower alkyl, lower alkoxy, halo(lower alkylthio), nitro, amino, lower alkylamino or di(lower alkyl) amino;
Z is methylene, oxygen, sulphur, sulphonyl, lower alkoxymethylene or a keto moiety;
A is a keto moiety or the moiety C(OH)R, wherein R is hydrogen or lower alkyl; and
a and b are each integers from 0 to 3,
in combination with a pharmaceutically acceptable non-toxic inert diluent or carrier.

52. A composition according to claim 51 wherein
X and Y are each fluoro, chloro, bromo, alkyl of 1 to 4 carbon atoms, alkoxy of 1 to 4 carbon atoms, haloalkylthio of 1 to 4 carbon atoms in the alkyl moiety and up to 5 halo atoms, nitro, amino, alkylamino of 1 to 4 carbon atoms, or dialkylamino of 1 to 4 carbon atoms;
R is hydrogen or alkyl of 1 to 4 carbon atoms; and
a and b are each integers from 0 to 2.

53. A composition according to claim 51 wherein
X and Y are each fluoro, chloro, bromo, methyl, ethyl, isopropyl, t-butyl, alkoxy of 1 or 2 carbon atoms, haloalkylthio of 1 or 2 carbon atoms in the alkyl moiety and up to 3 halo atoms selected from the group consisting of fluoro and chloro, nitro, amino, alkylamino of 1 or 2 carbon atoms or dialkylamino of 1 or 2 carbon atoms.

54. A composition according to claim 51 wherein
X and Y are each chloro, bromo or nitro;
Z is methylene, sulphonyl, alkoxymethylene of 1 to 4 carbon atoms in the alkoxy moiety or CO;
A is CO or the moiety C(OH)R, wherein R is hydrogen or alkyl of 1 to 4 carbon atoms;
a is 0 or 1; and
b is 0, 1 or 2.

55. A composition according to claim 54 wherein a and b are each 0.

56. A composition according to claim 54 wherein a is 1 and b is 0.

57. A composition according to claim 51 wherein the compound is a salt wherein said salt is selected from the group consisting of a hydrohalide, phosphate, nitrate, sulfate, acetate, maleate, succinate, fumarate, tartrate, citrate, salicylate, sorbate and 1,5-naphthalene disulfonate.

58. A composition according to claim 51 wherein the compound is

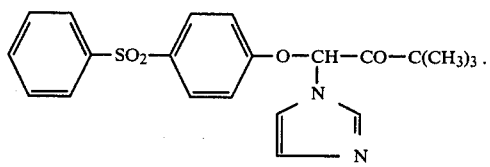

59. A composition according to claim 51 wherein the compound is

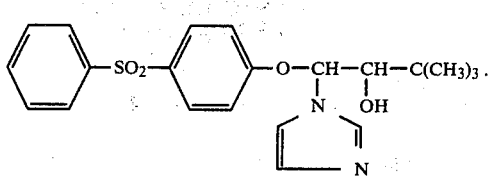

60. A composition according to claim 51 wherein Z is methylene, A is CO, and a and b are each 0.

61. A composition according to claim 51 wherein Z is oxygen, A is CO, and a and b are each 0.

62. A composition according to claim 51 wherein Z is oxygen, A is CO, and a and b are each 0, and the compound is in the form of the hydrochloride salt.

63. A composition according to claim 51 wherein Z is CO, A is CO and a and b are each 0.

64. A composition according to claim 51 wherein Z is methylene, A is CHOH, and a and b are each 0.

65. A composition according to claim 51 wherein Z is

a is CHOH and a and b are each 0.

66. A composition to claim 51 wherein Z is methylene.

67. A composition according to claim 51 wherein Z is methylene and a and b are each 0.

68. A composition according to claim 51 wherein Z is methylene, a is 0 and b is 1, 2 or 3.

69. A composition according to claim 51 wherein Z is methylene, a is 1, 2 or 3 and b is 0.

70. A composition according to claim 51 wherein Z is oxygen.

71. A composition according to claim 51 wherein Z is oxygen and a and b are each 0.

72. A composition according to claim 51 wherein Z is oxygen, a is 0 and b is 1, 2 or 3.

73. A composition according to claim 51 wherein Z is oxygen, a is 1, 2 or 3 and b is 0.

74. A composition according to claim 51 wherein Z is sulphur.

75. A composition according to claim 51 wherein Z is sulphur and a and b are each 0.

76. A composition according to claim 51 wherein Z is sulphur a is 0 and b is 1, 2 or 3.

77. A composition according to claim 51 wherein Z is sulphur, a is 1, 2 or 3 and b is 0.

78. A composition according to claim 51 wherein Z is sulphonyl.

79. A composition according to claim 51 wherein Z is sulphonyl, and a and b are each 0.

80. A composition according to claim 51 wherein Z is sulphonyl, a is 0 and b is 1, 2 or 3.

81. A composition according to claim 51 wherein Z is sulphonyl, a is 1, 2 or 3 and b is 0.

82. A composition according to claim 51 wherein Z is lower alkoxymethylene.

83. A composition according to claim 51 wherein Z is lower alkoxymethylene and a and b are each 0.

84. A composition according to claim 51 wherein Z is lower alkoxymethylene, a is 0 and b is 1, 2 or 3.

85. A composition according to claim 51 wherein Z is lower alkoxymethylene, a is 1, 2 or 3 and b is 0.

86. A composition according to claim 51 wherein Z is a keto moiety.

87. A composition according to claim 51 wherein Z is a keto moiety and a and b are each 0.

88. A composition according to claim 51 wherein Z is a keto moiety, a is 0 and b is 1, 2 or 3.

89. A composition according to claim 51 wherein Z is a keto moiety, a is 1, 2 or 3 and b is 0.

90. A composition according to claim 52 wherein a and b are each 0.

91. A composition according to claim 52 wherein a is 1 or 2 and b is 0.

92. A composition according to claim 52 wherein a is 0 and b is 1 or 2.

93. A composition according to claim 53 wherein a and b are each 0.

94. A composition according to claim 53 wherein a is 1 or 2 and b is 0.

95. A composition according to claim 53 wherein a is 0 and b is 1 or 2.

96. A composition according to claim 54 wherein a is 0 and b is 1 or 2.

97. A composition according to claim 54 wherein a is 1 and b is 0, 1 or 2.

98. A composition according to claim 57 wherein a and b are each 0.

99. A composition according to claim 57 wherein a is 0 and b is 1, 2 or 3.

100. A composition according to claim 57 wherein a is 1, 2 or 3 and b is 0.

101. A method of treating mycoses in humans and animals which comprises administering to a human or animal in need thereof an anti-mycotically effective amount of a compound of the formula

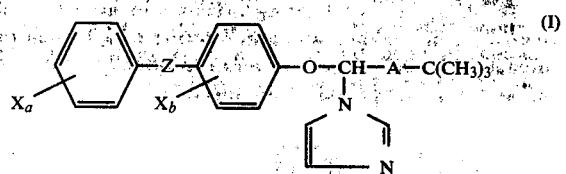

or a pharmaceutically acceptable, nontoxic salt thereof, wherein

X and Y are each halo, lower alkyl, lower alkoxy, halo(lower alkylthio), nitro, amino, lower alkylamino or di(lower alkyl)amino;

Z is methylene, oxygen, sulphur, sulphonyl, lower alkoxymethylene or a keto moiety;

A is a keto moiety or the moiety C(OH)R, wherein R is hydrogen or lower alkyl;

a and b are each integers from 0 to 3; and Z is a direct bond when A is the moiety C(OH)R as above defined, in combination with a pharmaceutically acceptable non-toxic inert diluent or carrier.

102. A method according to claim 101 wherein the compound is

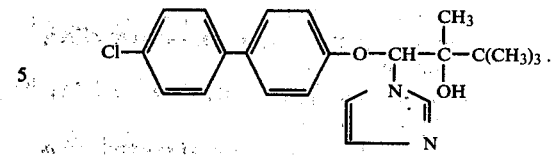

103. A method according to claim 101 wherein the compound is

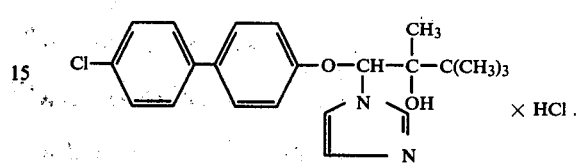

104. A method of treating mycoses in humans and animals which comprises administering to a human or animal in need thereof an antimycotically-effective amount of a compound of the formula

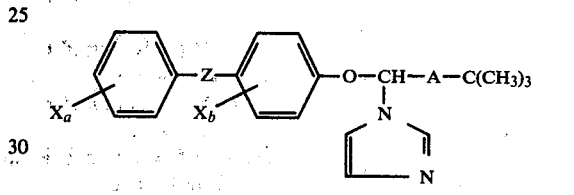

or a pharmaceutically acceptable, nontoxic salt thereof, wherein

X and Y are each halo, lower alkyl, lower alkoxy, halo(lower alkylthio), nitro, amino, lower alkylamino or di(lower alkyl)amino; Z is CO, A is CO and a and b are each O in combination with a pharmaceutically acceptable non-toxic inert diluent or carrier.

105. A method according to claim 101 wherein X is 4-chloro, Z is a direct bond, A is CHOH, a is 1 and b is 0.

106. A method according to claim 101 wherein X is 4-chloro, Z is a direct bond, A is CHOH, a is 1 and b is 0, and the compound is in the form of the sulphate salt.

107. A method according to claim 101 wherein X is 4-chloro, Z is a direct bond, A is CHOH, a is 1 and b is 0, and the compound is in the form of the hydrochloride salt.

108. A method according to claim 101 wherein X is 4-chloro, Z is a direct bond, A is CHOH, a is 1 and b is 0, and the compound is in the form of the phosphate salt.

109. A method according to claim 101 wherein X is 4-chloro, Z is a direct bond, A is CHOH, a is 1 and b is 0, and the compound is in the form of the nitrate salt.

110. A method according to claim 101 wherein Z is methylene.

111. A method according to claim 101 wherein Z is methylene and a and b are each 0.

112. A method according to claim 101 wherein Z is methylene, a is 0 and b is 1, 2 or 3.

113. A method according to claim 101 wherein Z is methylene, a is 1, 2 or 3 and b is 0.

114. A method according to claim 101 wherein Z is oxygen.

115. A method according to claim 101 wherein Z is oxygen and a and b are each 0.

116. A method according to claim 101 wherein Z is oxygen, a is 0 and b is 1, 2 or 3.

117. A method according to claim 101 wherein Z is oxygen, a is 1, 2 or 3 and b is 0.

118. A method according to claim 101 wherein Z is sulphur.

119. A method according to claim 101 wherein Z is sulphur and a and b are each 0.

120. A method according to claim 101 wherein Z is sulphur a is 0 and b is 1, 2 or 3.

121. A method according to claim 101 wherein Z is sulphur, a is 1, 2 or 3 and b is 0.

122. A method according to claim 101 wherein Z is sulphonyl.

123. A method according to claim 101 wherein Z is sulphonyl, and a and b are each 0.

124. A method according to claim 101 wherein Z is sulphonyl, a is 0 and b is 1, 2 or 3.

125. A method according to claim 101 wherein Z is sulphonyl, a is 1, 2 or 3 and b is 0.

126. A method according to claim 101 wherein Z is lower alkoxymethylene.

127. A method according to claim 101 wherein Z is lower alkoxymethylene and a and b are each 0.

128. A method according to claim 101 wherein Z is lower alkoxymethylene, a is 0 and b is 1, 2 or 3.

129. A method according to claim 101 wherein Z is lower alkoxymethylene, a is 1, 2 or 3 and b is 0.

130. A method according to claim 101 wherein Z is a keto moiety.

131. A method according to claim 101 wherein Z is a keto moiety and a and b are each 0.

132. A method according to claim 101 wherein Z is a keto moiety, a is 0 and b is 1, 2 or 3.

133. A method of treating mycoses in humans and animals which comprises administering to a human or animal in need thereof an antimycotically effective amount of a compound of the formula

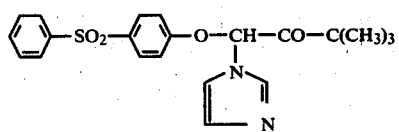

in combination with a pharmaceutically acceptable non-toxic inert diluent or carrier.

134. A method of treating mycoses in humans and animals which comprises administering to a human or animal in need thereof an antimycotically effective amount of a compound of the formula

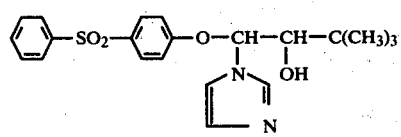

in combination with a pharmaceutically acceptable non-toxic inert diluent or carrier.

135. A method of treating mycoses in humans and animals which comprises administering to a human or animal in need thereof an anti-mycotically effective amount of a compound of the formula

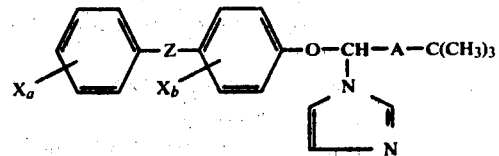

or a pharmaceutically acceptable, nontoxic salt thereof, wherein

X and Y are each halo, lower alkyl, lower alkoxy, halo(lower alkylthio), nitro, amino, lower alkylamino or di(lower alkyl)amino; Z is methylene, A is CO, and a and b are each 0 in combination with a pharmaceutically acceptable non-toxic inert diluent or carrier.

136. A method of treating mycoses in humans and animals which comprises administering to a human or animal in need thereof an antimycotically effective amount of a compound of the formula

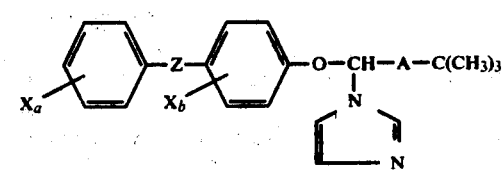

or a pharmaceutically acceptable, nontoxic salt thereof, wherein

X and Y are each halo, lower alkyl, lower alkoxy, halo(lower alkylthio), nitro, amino, lower alkylamino or di(lower alkyl)amino; Z is oxygen, A is CO, and a and b are each 0 in combination with a pharmaceutically acceptable non-toxic inert diluent or carrier.

137. A method according to claim 101 wherein Z is oxygen, A is CO, and a and b are each 0, and the compound is in the form of the hydrochloride salt.

138. A method of treating mycoses in humans and animals which comprises administering to a human or animal in need thereof an anti-mycotically effective amount of a compound of the formula

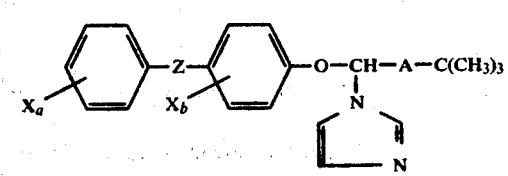

or a pharmaceutically acceptable, nontoxic salt thereof, wherein

X and Y are each halo, lower alkyl, lower alkoxy, halo(lower alkylthio), nitro, amino, lower alkylamino or di(lower alkyl)amino; Z is methylene, A is CHOH, and a and b are each 0 in combination with a pharmaceutically acceptable non-toxic inert diluent or carrier.

139. A method of treating mycoses in humans and animals which comprises administering to a human or animal in need thereof an anti-mycotically effective amount of a compound of the formula

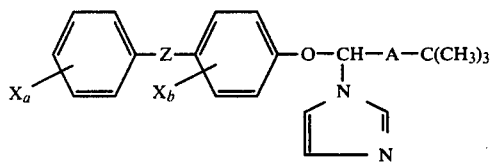 (I)
or a pharmaceutically acceptable, nontoxic salt thereof, wherein
X and Y are each halo, lower alkyl, lower alkoxy, halo(lower alkylthio), nitro, amino, lower alkylamino or di(lower alkyl)amino; Z is
A is CHOH and a and b are each 0 in combination with a pharmaceutically acceptable non-toxic inert diluent or carrier.
* * * * *